United States Patent
Staples, II et al.

(10) Patent No.: US 9,295,372 B2
(45) Date of Patent: Mar. 29, 2016

(54) MARKING AND TRACKING AN AREA OF INTEREST DURING ENDOSCOPY

(71) Applicant: CERNER INNOVATION, INC., Kansas City, KS (US)

(72) Inventors: Alan Harris Staples, II, Shawnee, KS (US); Karen Kaye Ramsey, Lenexa, KS (US); Bryan Michael Hunt, Blue Springs, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 171 days.

(21) Appl. No.: 14/030,653

(22) Filed: Sep. 18, 2013

(65) Prior Publication Data
US 2015/0078615 A1 Mar. 19, 2015

(51) Int. Cl.
*A61B 1/00* (2006.01)
*G06T 7/20* (2006.01)
*A61B 19/00* (2006.01)

(52) U.S. Cl.
CPC ........... *A61B 1/00039* (2013.01); *A61B 1/0005* (2013.01); *A61B 1/00009* (2013.01); *G06T 7/204* (2013.01); *A61B 2019/5291* (2013.01); *G06T 2207/10068* (2013.01); *G06T 2207/30032* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 5,497,776 A * | 3/1996 | Yamazaki ............... | A61B 8/12 128/916 |
| 5,944,655 A | 8/1999 | Becker | |
| 6,532,380 B1 * | 3/2003 | Close .................... | A61B 6/481 382/128 |
| 7,831,096 B2 * | 11/2010 | Williamson, Jr. ...... | A61B 19/52 382/128 |
| 8,149,236 B2 * | 4/2012 | Nakao .................... | A61B 6/466 345/419 |
| 8,248,414 B2 * | 8/2012 | Gattani ............... | A61B 1/00009 345/424 |
| 8,693,730 B2 * | 4/2014 | Umasuthan ............ | A61B 19/20 382/103 |
| 2005/0122343 A1 * | 6/2005 | Bailey ................... | G06T 3/0037 345/619 |
| 2008/0071142 A1 * | 3/2008 | Gattani ................ | A61B 1/0005 600/117 |
| 2008/0112604 A1 * | 5/2008 | Lloyd ..................... | A61B 5/06 382/131 |

(Continued)

FOREIGN PATENT DOCUMENTS

| EP | 2 014 791 A1 | 4/2009 |
|---|---|---|
| EP | 2 143 374 A1 | 1/2010 |

(Continued)

OTHER PUBLICATIONS

Endoscopic Real-Time Documentation System, Overview, eMerge Health Solutions, Copyright 2013, retrieved Sep. 18, 2013. http://www.emergehealth.com/#/.

(Continued)

*Primary Examiner* — Tsung-Yin Tsai
(74) *Attorney, Agent, or Firm* — Shook, Hardy & Bacon L.L.P.

(57) ABSTRACT

An area of interest of a patient's organ may be identified based on the presence of a possible lesion during an endoscopic procedure. The location of the area of interest may then be tracked relative to the camera view being displayed to the endoscopist in real-time or near real-time during the endoscopic procedure. If the area of interest is visually marked on the display, the visual marking is moved with the area of interest as it moves within the camera view. If the area of interest moves outside the camera view, a directional indicator may be displayed to indicate the location of the area of interest relative to the camera view to assist the endoscopist in relocating the area of interest.

20 Claims, 16 Drawing Sheets

(56) References Cited

U.S. PATENT DOCUMENTS

| | | | | |
|---|---|---|---|---|
| 2008/0207997 | A1* | 8/2008 | Higgins | A61B 1/00009 600/114 |
| 2009/0088897 | A1* | 4/2009 | Zhao | A61B 19/2203 700/250 |
| 2010/0036676 | A1* | 2/2010 | Safdi | G06F 19/321 705/2 |
| 2010/0039506 | A1* | 2/2010 | Sarvestani | A61B 19/5212 348/65 |
| 2010/0302358 | A1* | 12/2010 | Chen | A61B 5/0059 348/77 |
| 2012/0069167 | A1* | 3/2012 | Liu | G06T 7/0026 348/65 |
| 2012/0155731 | A1* | 6/2012 | Weersink | A61N 5/103 382/131 |
| 2012/0249737 | A1 | 10/2012 | Sood et al. | |
| 2012/0277527 | A1 | 11/2012 | Sood et al. | |
| 2012/0307027 | A1* | 12/2012 | Popovic | A61B 19/2203 348/65 |
| 2013/0165753 | A1* | 6/2013 | Takahashi | A61B 1/05 600/109 |
| 2013/0204084 | A1* | 8/2013 | Hale | A61B 5/04525 600/109 |
| 2013/0218024 | A1* | 8/2013 | Boctor | A61B 8/4254 600/476 |
| 2014/0046131 | A1* | 2/2014 | Morita | A61B 1/00179 600/109 |
| 2015/0073265 | A1* | 3/2015 | Popovic | A61B 1/0005 600/424 |

FOREIGN PATENT DOCUMENTS

| | | |
|---|---|---|
| EP | 2 401 954 A1 | 4/2012 |
| WO | WO 9528872 | 11/1999 |
| WO | WO 2009002467 A2 | 12/2008 |
| WO | WO 2009003225 A1 | 1/2009 |
| WO | WO 2010060039 A2 | 5/2010 |
| WO | WO 2012014438 A1 | 7/2011 |

OTHER PUBLICATIONS

Endoscopic Real-Time Documentation System, Features, eMerge Health Solutions, Copyright 2013, retrieved Sep. 18, 2013. http://www.emergehealth.com/endodcopic-real-time-workflow-systems/features/.

Meining A., et al., Eye-tracking for assessment of image perception in gastrointestinal endoscopy with marrow-band imaging compared with white-light endoscopy, Endoscopy, 2010; 42: 652-655, http://citeseerx.ist.psu.edu/viewdoc/download?doi=10.1.1.176.2818&rep=rep1&type=pdf.

Martinez, Fidel, Google Street View for Colonoscopy Tool, McMaster University in Canada, Mar. 20, 2013, http://www.dailydot.com/news/google-street-view-colonoscpy-tool/.

First Action Interview Pre-Interview Communication dated Mar. 23, 2015 in U.S. Appl. No. 14/030,643, 10 pages.

Non-Final Office Action dated Jul. 15, 2015 in U.S. Appl. No. 14/030,643, 13 pages.

* cited by examiner

MARKING AND TRACKING AN AREA OF INTEREST DURING ENDOSCOPY

CROSS-REFERENCE TO RELATED APPLICATIONS

This application is related by subject matter to the invention disclosed in U.S. application Ser. No. 14/030,643, filed on even date herewith, entitled "LESION DETECTION AND IMAGE STABILIZATION USING PORTION OF FIELD OF VIEW," which is assigned or under obligation of assignment to the same entity as this application, and incorporated in this application by reference.

BACKGROUND

One of the key challenges in endoscopy is maintaining sufficiently high quality of screening. Quality for endoscopy is generally defined in part on whether the endoscopist found all lesions that may be of interest during an endoscopic procedure. This may include, for instance, lesions that may be cancerous or pre-cancerous. Various societies debate on different approaches to endoscopic procedures and different ways to evaluate performance of endoscopists. However, these debates have done little to actually improve the level of quality of endoscopic procedures.

BRIEF SUMMARY

Embodiments of the present invention relate to techniques that may be employed to assist endoscopists in improving the quality of endoscopic procedures. In accordance with some embodiments, an area of interest within a patient's organ may be identified during an endoscopic procedure. The area of interest may generally correspond with an area of the patient's organ that may contain a lesion. The location of the area of interest relative to the camera view provided by the endoscope may then be tracked in real-time or near real-time during the endoscopic procedure. If a visual marker is used on a display to mark the area of interest, the visual marker is moved with the area of interest if the area of interest moves within the camera view. If the area of interest moves outside the camera view, a directional indication is displayed to indicate to the endoscopist the location of the area of interest relative to the camera view to assist the endoscopist in relocating the area of interest.

Accordingly, in one aspect, an embodiment of the present invention is directed to one or more computer storage media storing computer usable instructions that, when used by one or more computing devices, cause the one or more computing devices to perform operations. The operations include identifying an area of interest of a patient's organ within images captured during an endoscopic procedure and providing a visual marker identifying the area of interest within displayed images of a camera view being viewed by an endoscopist. The operations also include tracking a location of the area of interest relative to the camera view during the endoscopic procedure and determining the location of the area of interest has changed relative to the camera view. The operations further include determining if the area of interest remains within the camera view. If the area of interest remains within the camera view, the operations include moving the visual marker based on the change in the location of the area of interest. If the area of interest has moved outside of the camera view, the operations includes providing a visual directional marker based on the location of the area of interest relative to the camera view.

In another embodiment, an aspect is directed to a method in a clinical computing environment for tracking an area of interest of a patient's organ during an endoscopic procedure. The method includes identifying the area of interest within a camera view during the endoscopic procedure. The method also includes determining the area of interest has moved outside the camera view during the endoscopic procedure. The method further includes displaying a directional indication on displayed images identifying a location of the area of interest relative to the camera view during the endoscopic procedure.

A further embodiment is directed to a system in a clinical computing environment for tracking an area of interest of a patient's organ during an endoscopic procedure. The system includes one or more processors. The system also includes one or more computer storage media storing instructions to cause the one or more processors to: identify the area of interest within a camera view during the endoscopic procedure, determine the area of interest has moved outside the camera view during the endoscopic procedure, and display a directional indication on displayed images identifying a location of the area of interest relative to the camera view during the endoscopic procedure.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein.

DETAILED DESCRIPTION

Figure 1:
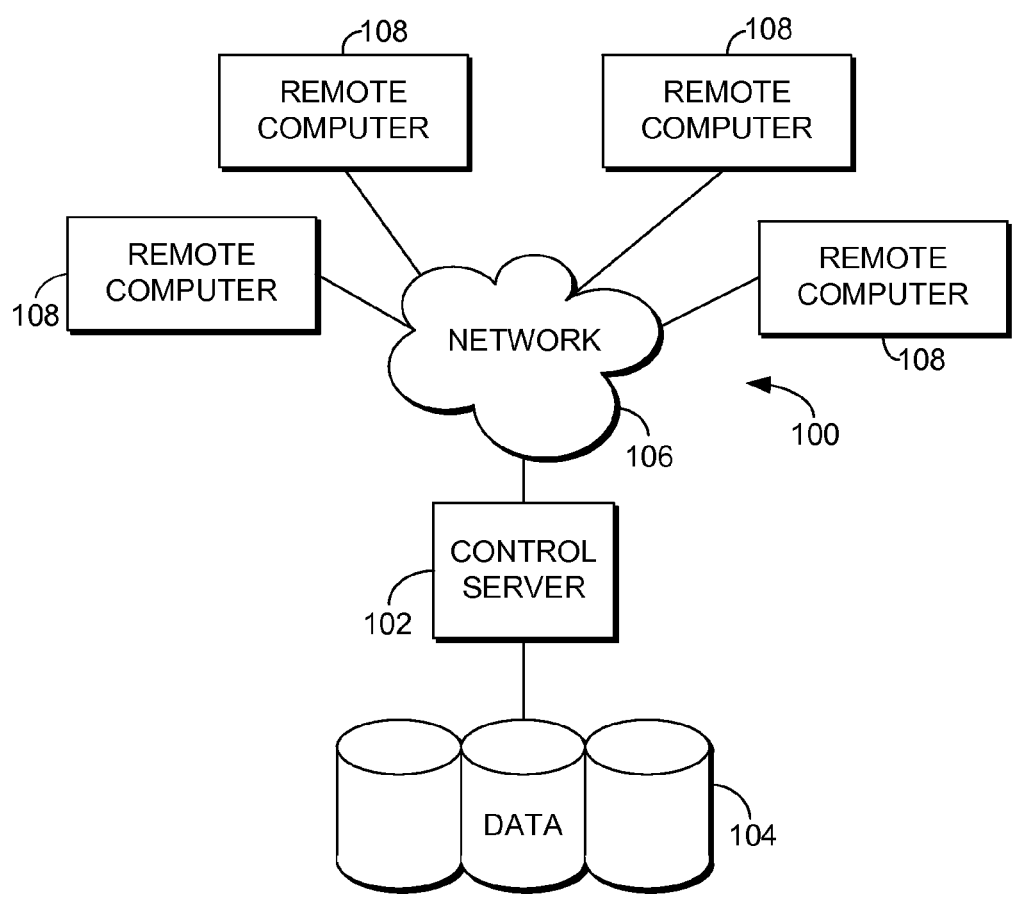
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide techniques to assist endoscopists in improving the quality of endoscopic procedures. Unless otherwise indicated, these techniques may be employed in real-time or near real-time during an endoscopic procedure to assist the endoscopist during the endoscopic procedure. In accordance with some embodiments, computer vision techniques may be employed to help detect, mark, and track lesions in real-time or near real-time during an endoscopic procedure. Generally, any known computer vision techniques may be employed within the scope of embodiments of the present invention to analyze video images captured by an endoscope during an endoscopic procedure. The images analyzed may include 2D images and/or 3D images captured using known 3D imaging techniques (e.g., stereoscopy, time-of-flight, structured light, etc.).

The computer visions techniques employed may analyze video images captured during an endoscopic procedure and perform object recognition to identify possible lesions. As used herein, the term "lesion" refers broadly to any abnormality in the tissue of an organ. Identified lesions may be visually marked on the endoscope camera view displayed to the endoscopist performing the endoscopic procedure to allow the endoscopist to identify the lesions.

Additionally, the computer vision techniques may track the location of an identified lesion relative to the camera view displayed to the endoscopist using, for instance, object recognition/tracking and motion estimation techniques. This may include lesions automatically identified by the system and lesions manually identified by the endoscopist. By tracking the location of a lesion within a camera view, any visual marking provided for the lesion may be moved with the lesion as the lesion moves around the camera view. Additionally, motion estimation techniques may be employed to estimate the location of a lesion relative to the camera view when the lesion moves outside of the camera view to assist endoscopists in relocating the lesions. Directional information may be displayed to the endoscopist to provide an indication of the location of the lesion relative to the camera view to assist the endoscopist in relocating the lesion.

Further embodiments of the present invention employ an endoscope camera with an overall field of view (FOV) but present only a portion of the overall FOV to the endoscopist. In such embodiments, the overall FOV may be used for lesion detection purposes by the system. In other words, while only a portion of the FOV is presented to the endoscopist, the system may analyze the entire FOV for lesions and provide a notification of any detected lesions to the endoscopist's attention. The overall FOV may also be used for image stabilization purposes. More particularly, when a lesion has been identified (either automatically by the system or manually by the endoscopist), the lesion may be maintained with the camera view displayed to the endoscopist even when the lesion moves relative to the endoscope camera by changing the displayed portion of the overall FOV.

Additional techniques may be employed to help navigate an endoscope through the lumen (i.e., hollow center) of a patient's organ, for instance, for advancing the endoscope through the organ. This may include using computer vision to identify the center of the lumen and employing mechanical controls on the camera end of the endoscope to maintain the endoscope end near the center of the lumen. Additionally or alternatively, the endoscopist's eyes looking the displayed camera view may be tracked using known eye/head tracking techniques, and mechanical controls may be employed to adjust the position/directionality of the endoscope end based on the endoscopist's eye movements Still further embodiments of the present invention may employ image stitching techniques to stitch together images captured during an endoscopic procedure to generate photo-realistic model of the patient's organ. The generated organ model may be used for a variety of purposes, including assisting the endoscopist in navigating to identified lesions and determining locations of the organ that have not been imaged.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. Endoscopists may include, but are not limited to, any clinician performing, participating in, or otherwise associated with an endoscopic procedure. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Lesion Detection and Marking

Some embodiments of the present invention are directed to identifying areas of interest within a patient's organ during an endoscopic procedure. The area of interest may generally include a lesion or possible lesion that may require further analysis, treatment, or other clinical attention. In some instances, an area of interest may be manually identified by an endoscopist. In other instances, computer vision techniques may be employed by the system to automatically identify an area of interest, which is then brought to the endoscopist's attention. An area of interest may be visually marked on the display to allow the endoscopist to quickly recognize the area. Additionally, metadata about the area of interest may be stored by the system.

Figure 2:
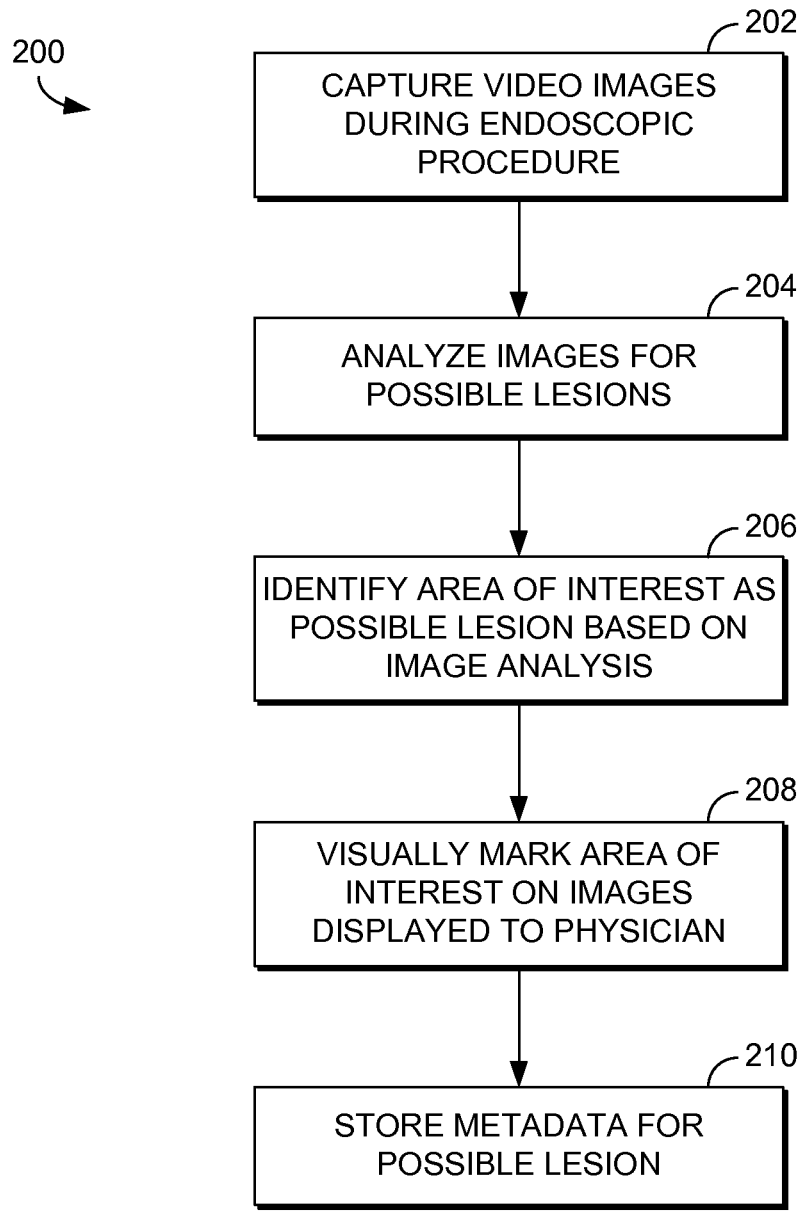
FIG. 2 is a flow diagram showing a method for identifying and marking an area of interesting potentially containing a lesion during an endoscopic procedure on a patient in accordance with an embodiment of the present invention.

Referring to FIG. 2, a flow diagram is provided that illustrates a method 200 for identifying and marking an area of interest containing a possible lesion in real-time or near real-time during an endoscopic procedure on a patient in accordance with an embodiment of the present invention. Initially, as shown at block 202, video images are captured using an endoscope during an endoscopic procedure. Video images are analyzed by the system in real-time or near real-time during the endoscopic procedure to detect possible lesions in the images, as shown at block 204.

Lesion detection may be performed using any of a number of different computer vision techniques in accordance with various embodiments of the present invention. By way of example only and not limitation, in some embodiments, the system maintains a library of shapes for different lesion types. The library may be manually generated or may be algorithmically generated, for instance, by training the library using various images of different lesion types. The system may employ the library to identify regions of a patient's organ that may match one or more of the shapes. For instance, the system may perform edge detection or other image analysis to identify shapes of objects or regions within the patient's organ. The identified shapes from the analyzed images are compared against the library of lesion shapes to determine if any matches are found. In some embodiments, matching may be based on a probability determination and only objects/regions that have a probability exceeding some threshold are identified as matches.

Based on the image analysis, an area of the patient's organ is identified by the system as an area of interest containing a possible lesion, as shown at block 206. Based on the identification, the area is visually marked on images being displayed to the endoscopist, as shown at block 208. Any visual indication that draws the endoscopist's attention to the identified area of interest may be employed. By way of example only and not limitation, this visual indication may include: placing a box around the area, highlighting around the edge of the area, coloring the area, and/or de-emphasizing the image outside the area (e.g., dimming everything except the area of interest), to name a few.

Figure 3A:
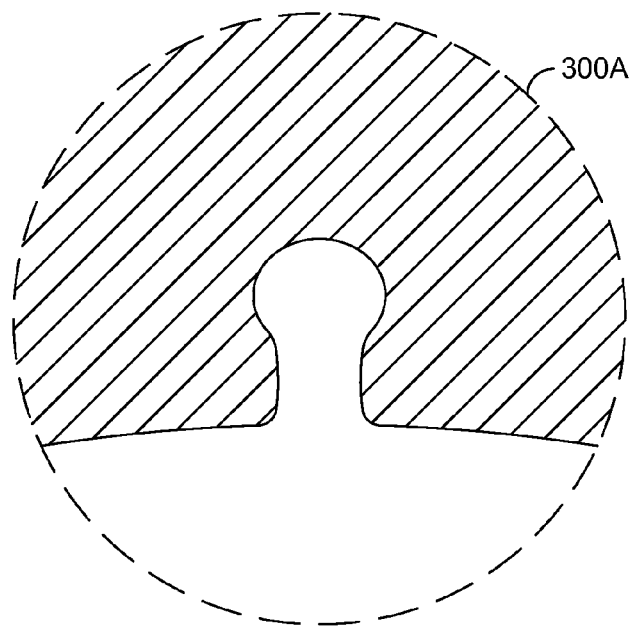
FIGS. 3A and 3B are example screenshots illustrating the automatic detection and marking of a possible lesion.
Figure 3B:
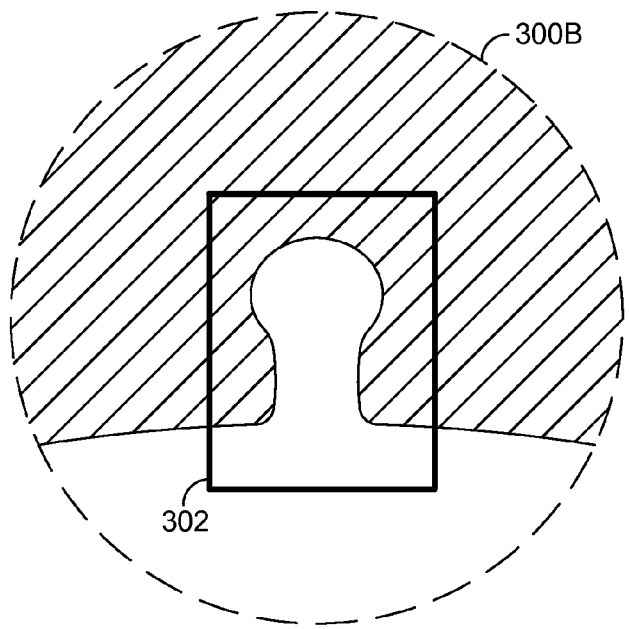

FIGS. 3A and 3B are example screenshots illustrating the automatic detection and marking of a possible lesion. Initially, FIG. 3A provides an example screenshot of a video image 300A displayed to the endoscopist during an endoscopic procedure. The screenshot of FIG. 3A shows an image before detection of a possible lesion. After a possible lesion is detected, a box 302 is placed around the area of the patient's organ detected as a possible lesion, as shown in the video image 300B of FIG. 3B. As noted above, other forms of marking the possible lesion may be employed and the box show in FIG. 3B is provided by way of example only and not limitation.

Referring again to FIG. 2, metadata is stored about the possible lesion, as shown at block 210. The metadata may include any information that may be useful for tracking and/or recording information about the lesion. The metadata may be automatically identified and stored by the system and/or the metadata may be manually entered by an endoscopist. The metadata may include, for instance, an image of the area (single image or video). The metadata may also include a relative location of the area (e.g., sigmoid colon, cecum, distance into organ, etc.). The metadata may also include information regarding what triggered identification of the possible lesion. The metadata may further include a lesion type. For instance, a library of shapes maintained by the system used for identification purposes may indicate of type of lesion with various lesion shapes. Accordingly, the lesion type may be automatically determined based on the shape that triggered the identification by the system. Alternatively, the endoscopist may manually identify the lesion type. Additional notes about the possible lesion may be provided by the endoscopist and stored as metadata. Manually entered metadata may be provided via any type of available input, such as, for instance, voice recording (with or without voice-to-text), text entry, etc.

In some embodiments, the endoscopist performing the endoscopy may view the area identified by the system and decide whether to store metadata for the area. For instance, the endoscopist may review the identified area and decide that the area is not a potential lesion. Alternatively, the endoscopist may review the identified area and decide the area is a potential lesion. In some embodiments, after identifying an area as a potential lesion and marking the area, the system may prompt the endoscopist to confirm the area as a potential lesion. Metadata may be stored in response to the endoscopist confirming the area as a potential lesion. In other embodiments, the endoscopist may select to store metadata for a possible lesion without any prompting, for instance, by clicking a button on the endoscope or an associated computing device being used during the endoscopic procedure.

As noted above, while shape detection is one approach for the system to automatically identify an area of interest as a possible lesion, other methods for detecting possible lesions may be employed within the scope of embodiments of the present invention. In some embodiments, lesion detection by the system may employ image enhanced endoscopy. As used herein, "image enhanced endoscopy" includes viewing/analyzing images from an endoscopic procedure by modifying one or more color channels. This may or may not include use of dyes in the patient's organ. As is known in the art, some lesions may be better detected by viewing coloration of organs under modified color conditions, as opposed to viewing the patient's organ under normal white light. Accordingly, the system may analyze images under different color conditions in some embodiment to assist in lesion detection.

Figure 4:
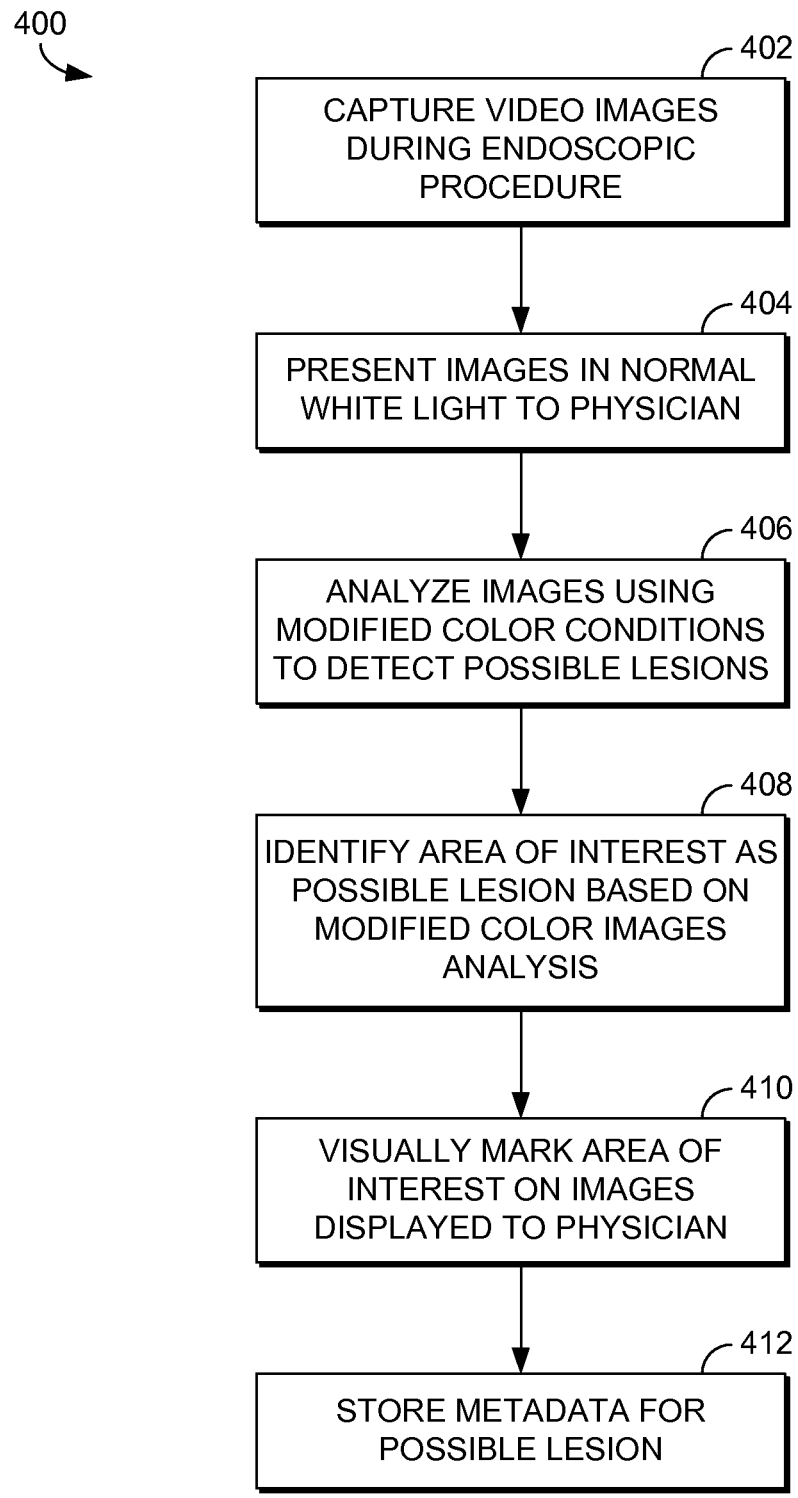
FIG. 4 is a flow diagram showing a method for employing image enhanced endoscopy as a background process in real-time or near real-time during an endoscopy procedure in accordance with an embodiment of the present invention.

Some embodiments may employ image enhanced endoscopy as a background process for lesion detection while presenting video images to the endoscopist. For instance, video images may be presented in white light to the endoscopist, while the system may analyze images with modified color conditions as a background process during the endoscopic procedure for automatic lesion detection. With reference to FIG. 4, a flow diagram is provided that illustrates a method 400 for employing image enhanced endoscopy as a background process in real-time or near real-time during an endoscopic procedure in accordance with an embodiment of the present invention. Initially, as shown at block 402, video images are captured using an endoscope during an endoscopic procedure on a patient.

Video images are presented to the endoscopist in normal white light, as shown at block 404. Additionally, video images are analyzed by the system in real-time or near real-time under modified color conditions as a background process during the endoscopic procedure to detect possible lesions in the images, as shown at block 406. In various embodiments, images under the modified color conditions used by the system for automatic lesion detection may or may not be presented to the endoscopist in addition to the white light images. In some cases, only the white light images are presented to the endoscopist and the modified color images are only analyzed by the system in the background without being displayed. In other cases, the modified color images may also be presented. For instance, the modified color channel images may be presented as separate images (either on the same screen or separate screen) or may be presented as a picture-in-picture with the white light images.

Color channels may be modified for analysis purposes in a variety of different ways within the scope of embodiments of the present invention. In some instance, only a single modified color setting may be employed, while in other instances, multiple modified color settings may be employed. The modified color settings may include discrete color channel settings. Alternatively, the color channels may be variably changed to assist in lesion detection. Any and all such combinations and variations are contemplated to be within the scope of embodiments of the present invention.

Analysis of the modified color channel images by the system for lesion detection may include looking for particular color patterns but may also include other lesion detection approaches. For instance, shape detection (such as that described above with reference to FIG. 2) may be employed in conjunction for lesion detection. Any and all such combinations and variations are contemplated to be within the scope of embodiments of the present invention.

An area of the patient's organ is identified as a possible lesion by the system based on the modified color image analysis, as shown at block 408. Based on the identification, the area is visually marked on a video being displayed to the endoscopist, as shown at block 410. This may include marking the area on the white light images being displayed and/or marking the area on modified color images if also being presented to the endoscopist. As discussed with reference to FIG. 2, any visual indication that draws the endoscopist's attention to the identified area of interest may be employed (e.g., boxing around the area, highlighting the edges of the area, etc.).

In some embodiments, when a possible lesion is detected using modified color images, the white light images being displayed to the endoscopist may be automatically changed to modified color images to help the endoscopist identify the area as a possible lesion. In other embodiments, the system may not automatically change the display but may instead provide some indication to the endoscopist that the area was detected using modified color images. The endoscopist may then manually select to view the video images being displayed using the modified color channel used by the system to automatically identify the area of interest as a possible lesion.

Metadata is stored about the possible lesion, as shown at block 412. In some embodiments, the metadata may be automatically stored, while in other embodiments the metadata may be stored in response to a confirmation from the endoscopist that the area is a possible lesion. The metadata may include any information that may be useful for tracking and/or recording information about the lesion. This may include, for instance, the metadata discussed above with reference to FIG. 2. Additionally, the metadata may include information about the modified color setting using to identify the possible lesion. The metadata could also include images (still and/or video) under the modified color.

Lesion Tracking and Relocation

After an area of interest has been identified based on the presence of a lesion or possible lesion, the area of interest may be tracked by the system. The area of interest may be identified manually by the endoscopist or automatically by the system. The tracking may include employing computer vision techniques, such as those described above, to recognize shapes and/or colors for orientation purposes. By tracking an area of interest, the system may be able to assist the endoscopist in viewing and/or relocating the area of interest. For instance, after a lesion has been detected, an endoscopist may need to pass something, such as forceps or a snare, down the channel of the endoscope. Sometimes during this process, the end of the endoscope may move causing the lesion to move out of view and time must be spent to relocate the lesion. Accordingly, some embodiments employ techniques to help track a location of an area of interest relative to the camera view provided by the endoscope to assist that endoscopist in relocating the area of interest to bring the area of interest back within the camera view.

Figure 5:
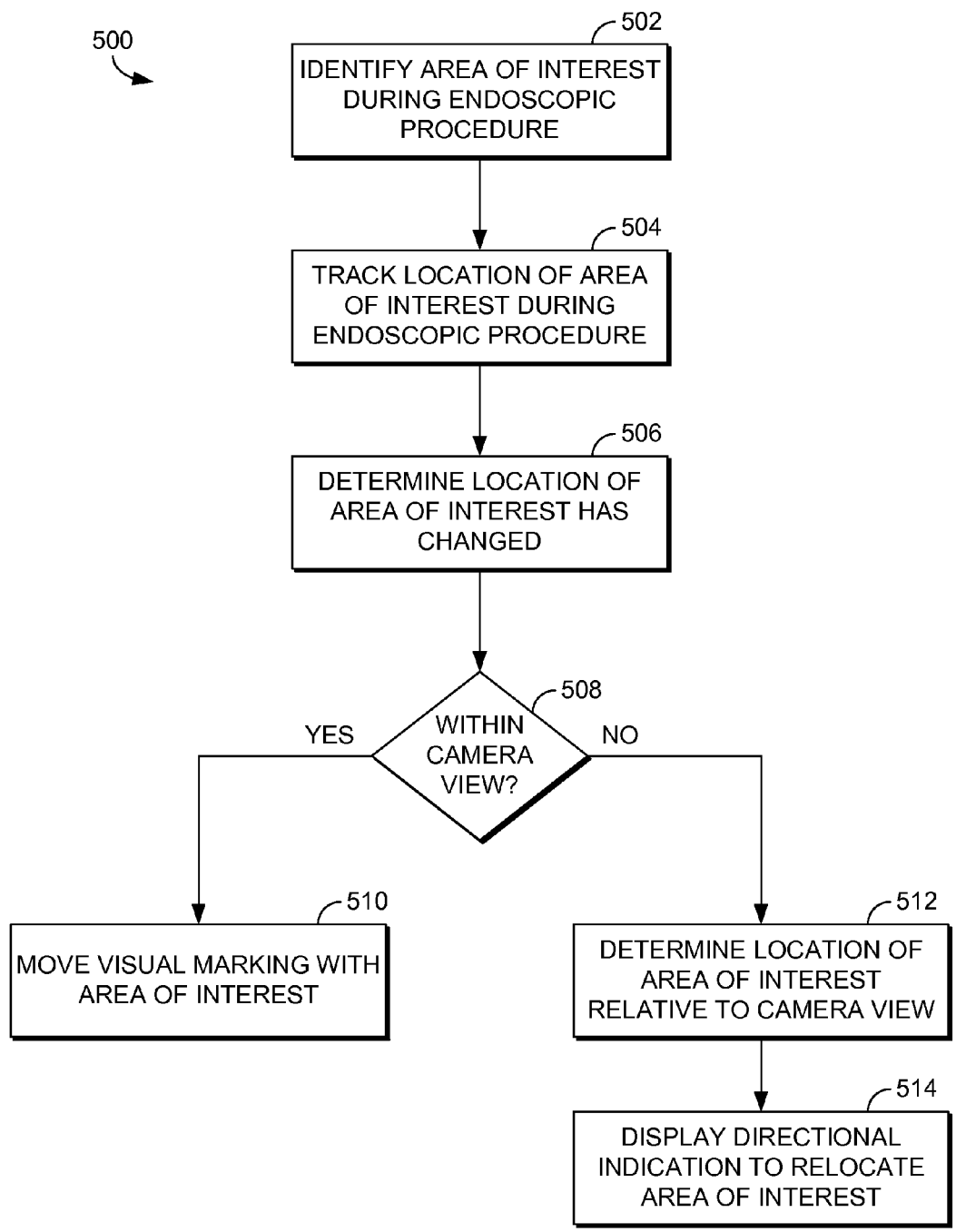
FIG. 5 is a flow diagram showing a method for tracking an area of interest in real-time or near real-time during an endoscopic procedure in accordance with an embodiment of the present invention.

With reference now to FIG. 5, a flow diagram is provided that illustrates a method 500 for tracking an area of interest in real-time or near real-time during an endoscopic procedure in accordance with an embodiment of the present invention. Initially, an area of interest that may contain a possible lesion is identified during an endoscopic procedure, as shown at block 502. The area of interest may be automatically identified by the system (with or without an endoscopist confirmation) as discussed above, for instance, with reference to FIGS. 2 and 4. Alternatively, the area of interest may be one that was manually identified by the endoscopist without any automatic detection by the system. For instance, the system may display images captured by the endoscope during the endoscopic procedure and provide tools to allow the endoscopist to manually mark an area as an area of interest. This may include, for example, allowing the endoscopist to employ a mouse or other input device to mark an area on displayed images as an area of interest. The endoscopist could draw an outline around the edges of the area of interest or simply draw a box around the area.

The location of the identified area of interest relative to the camera view is tracked during the endoscopic procedure, as shown at block 504. In particular, as the camera is moved during the endoscopic procedure, the system continues to track where the area of interest is relative to the image being displayed to the endoscopist. The tracking may be performed by repeatedly analyzing the video images to track the area of interest while the area of interest remains within the camera view and also analyzing the video images to determine the location of the area of interest relative to the camera view when the area of interest moves outside the camera view. The analysis may include shape detection, detection via image-enhanced endoscopy, and other computer vision techniques. These computer vision techniques may generally determine the movement of the camera view relative to the area of interest, for instance, by determining the relative direction shapes are moving within the camera view.

Figure 6A:
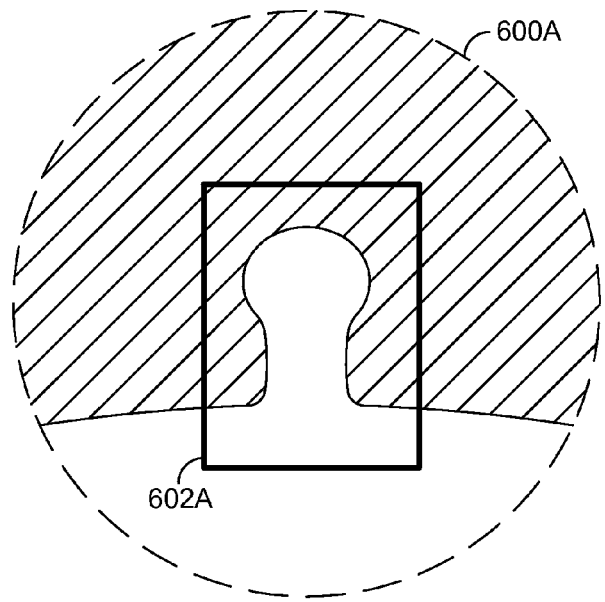
FIGS. 6A-6D are example screenshots illustrating tracking an identified area of interest in real-time or near real-time during an endoscopic procedure.
Figure 6B:
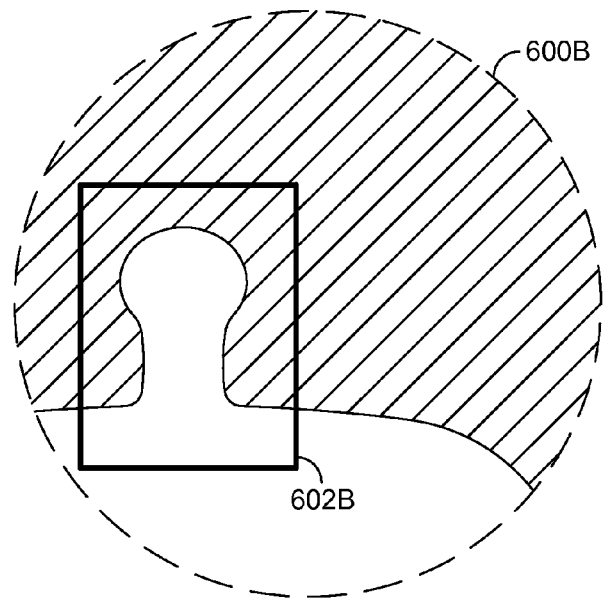

Based on the tracking, it is determined that the location of the area of interest has changed, as shown at block 506. A determination is also made regarding whether the area of interest remains within the camera view, as shown at block 508. If the area of interest remains within the camera view and the area of interest is visually marked (e.g., using a box or other indication as discussed above), the visual marking is moved with the area of interest as the area of interest is moved within the camera view, as shown at block 510. By way of example, FIG. 6A illustrates an area of interest marked with a box 602A near the center of the camera view 600A. As shown in FIG. 6B, as the area of interest moves to the left side of the camera view 600B (i.e., the camera has moved to the right relative to the area of interest), the system continues to track the area of interest, and the box 602B moves with the area of interest.

Figure 6C:
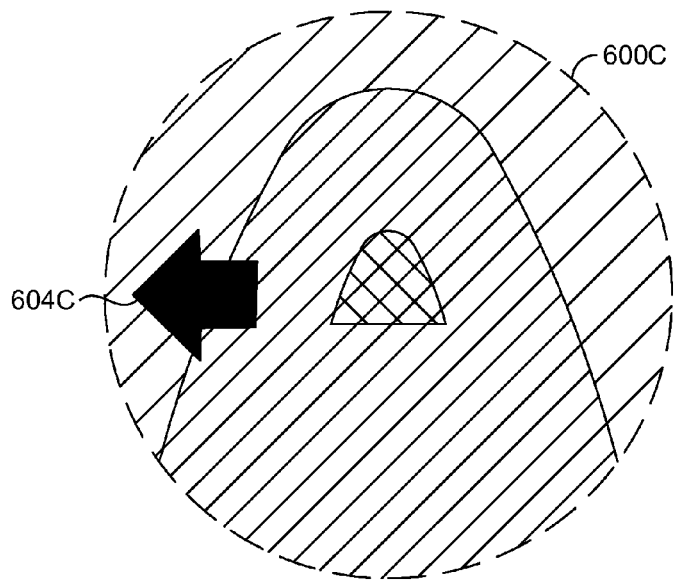

If the system determines the area of interest has moved outside of the camera view, the system determines a location of the area of interest relative to the camera view, as shown at block 512. Additionally, the system may provide a directional indication displayed to the endoscopist to help the endoscopist relocate the area of interest, as shown at block 514. For instance, by analyzing the video images, the system may recognize that an area of interest has initially moved to the left side of the camera view (e.g., as shown in FIG. 6B). As the camera continues to move to the right, the system may continue to analyze the video images and recognize when the area of interest has moved off the left side of the camera view. When this occurs, the system may display directional information to assist the endoscopist. For instance, FIG. 6C is a screenshot that illustrates a directional arrow 604C that indicates that the area of interest is to the left of the camera view 600C. If the endoscopist wishes to view the area of interest again, the directional arrow 604C indicates to the endoscopist to move the endoscope camera to the left to relocate the lesion.

Figure 6D:
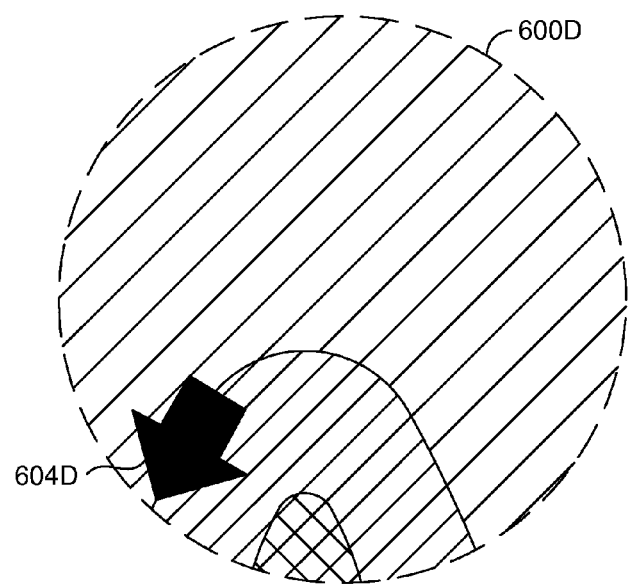

As the camera continues to be moved, the system may continue to analyze video images for orientation purposes. For instance, by detecting shapes within the video images and monitoring the movements of the shapes, the system can determine the directional movements of the camera. Based on these movements, the system may continue to determine the location of the area of interest relative to the camera view while the area of interest is outside of the camera view. For instance, suppose after the camera has moved to the right (causing the area of interest to move off the left side of the camera view as in FIG. 6C), the camera is moved up. The system may determine the upward movement by analyzing the video images to recognize shapes within the camera view and recognize that the shapes are moving downward in the camera view as the camera moves up. As a result, the system may recognize that the area of interest is now to the left and down from the camera view. As a result, the system may display a directional arrow 604D in the camera view 600D that points diagonally to the left and down, as shown in the example screenshot provided in FIG. 6D. In some embodiments, the endoscope may be equipped with additional components (e.g., gyroscope, accelerometer, RFID, GPS, etc.) that may assist in tracking the movement of the endoscope camera and determining the location of the area of interest relative to the camera view.

As noted above, tracking the location of an area of interest relative to a camera view may assist an endoscopist in viewing the area of interest as it moves within the camera view and relocating the area of interest if it moves outside the camera view. The time an area of interest spends outside the camera view before it is relocated may also be monitored. This may provide information regarding how long it took the endoscopist to relocate the area of interest. The relocation time may be stored and used for analytics purposes.

Lesion Detection and Tracking Using Large FOV

Some embodiments of the present invention operate using a camera having a field of view (FOV) that matches or closely matches the images displayed to the endoscopist. The FOV of view often used for endoscopy is typically within the range of 140 degrees to 170 degrees. A FOV smaller than this range may be less desirable as the endoscopist is presented with a smaller viewable area. A FOV larger than this range (e.g., using a fisheye lens) may also be less desirable because the larger FOV may result in image/spatial distortion that may be distracting to the endoscopist and make it more difficult for the endoscopist to detect lesions.

Figure 7A:
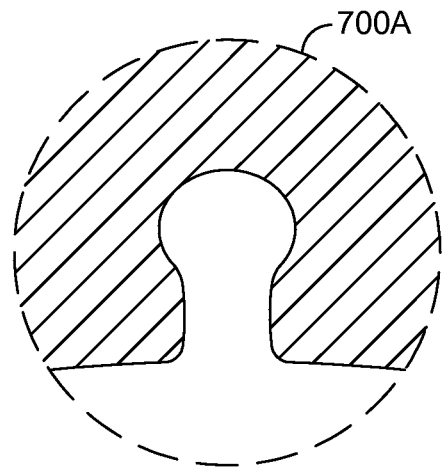
FIGS. 7A and 7B are diagrams illustrating a traditional FOV and a larger FOV with only a portion of the larger FOV displayed.
Figure 7B:
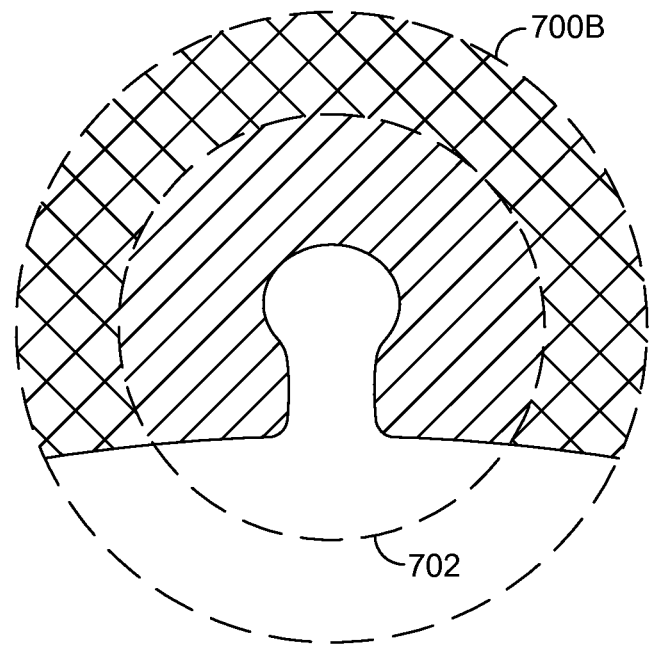

In accordance with some embodiments of the present invention, a camera with a particular FOV (e.g., greater than 170 degrees) is employed. However, only a portion of the overall camera FOV is presented to the endoscopist. For instance, the portion of the overall FOV may be within the 140 degrees to 170 degrees range discussed above. By way of example, FIG. 7A illustrates a camera with a traditional FOV 700A in the 140 to 170 degrees range. In contrast, FIG. 7B illustrates a camera with a larger FOV 700B (e.g., 220 degrees). However, in accordance with some embodiments of the present invention, the entire FOV from the camera in FIG. 7B is not displayed to the endoscopist. Instead, only a portion of the overall FOV 700B is displayed. The portion of the overall FOV 700B displayed to the endoscopist is shown by the area 702 in FIG. 7B. As can be seen from FIGS. 7A and 7B, the displayed portion 702 from FIG. 7B matches the camera view provided by the overall FOV 700A from FIG. 7A. For instance, the displayed portion 702 may have a FOV of 170 degrees or less (e.g., within the traditional 140 to 170 degrees range). As such, additional area is captured using the approach in FIG. 7B, but an area matching a traditional camera view is displayed.

A number of advantages may be realized by using a camera with a larger FOV but only displaying a portion of the overall FOV to the endoscopist. By only displaying a portion of the overall FOV to the endoscopist, the image/spatial distortion issue of the larger FOV may be alleviated. Additionally, in some embodiments, the larger FOV may be employed for lesion detection purposes. In particular, although some portions of the larger FOV are not displayed to the endoscopist, the system may analyze those non-displayed portions to detect possible lesions and bring identified areas of interest to the endoscopist's attention.

Figure 8:
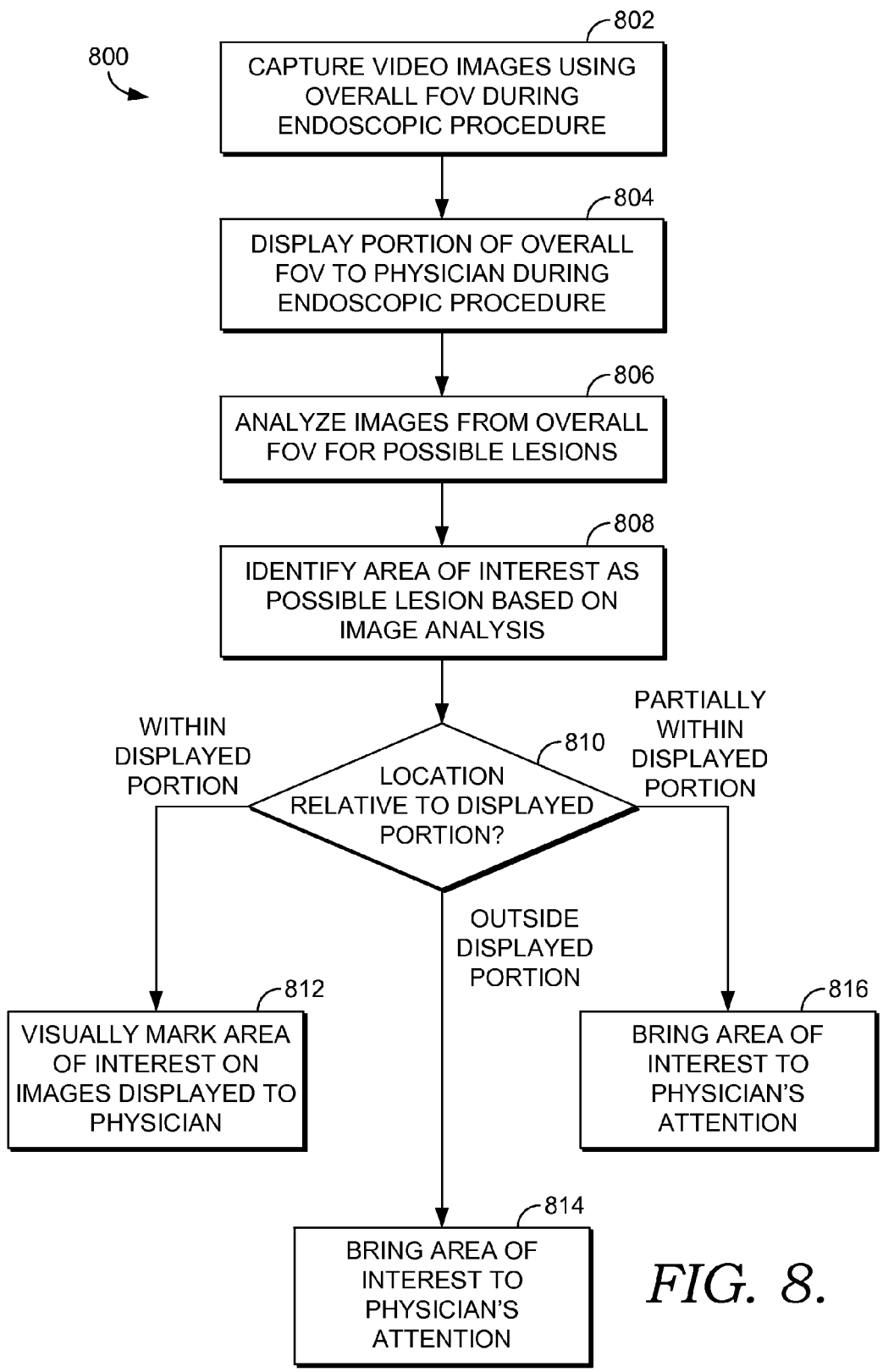
FIG. 8 is a flow diagram showing a method for using a larger FOV for lesion detection while only presenting a portion of the overall FOV to the endoscopist in accordance with an embodiment of the present invention.

Turning to FIG. 8, a flow diagram is provided that illustrates a method 800 for using an overall FOV for lesion detection while only presenting a portion of the overall FOV to the endoscopist in accordance with an embodiment of the present invention. As shown at block 802, video images are captured using a camera with an overall FOV during an endoscopic procedure. In some embodiments, this overall FOV may be greater than 170 degrees and may be 220 degrees in some particular embodiments.

A portion of the overall FOV is displayed to the endoscopist in real-time or near real-time during the endoscopic procedure, as shown at block 804. In some embodiments, this may be the center portion of the overall FOV (e.g., as shown in FIG. 7B). Video images from the overall FOV are also analyzed by the system in real-time or near real-time during the endoscopic procedure to detect possible lesions in the images, as shown at block 806. An area of the patient's organ is identified as a possible lesion by the system based on the image analysis, as shown at block 808.

The area of interest containing the possible lesion identified by the system may be entirely within the displayed portion of the overall FOV, entirely outside the displayed portion of the overall FOV, or may be partially within the displayed portion and partially outside the displayed portion. Accordingly, the system determines the location of the area of interest relative to the displayed portion of the overall FOV, as shown at block 810.

If the entire area of interest is within the displayed portion, the area is visually marked on the video being displayed to the endoscopist, as shown at block 812. Any visual indication that draws the endoscopist's attention to the area of interest may be employed, such as those discussed above (e.g., box around the area of interest, highlighting an edge of the area of interest, etc.).

Figure 9:
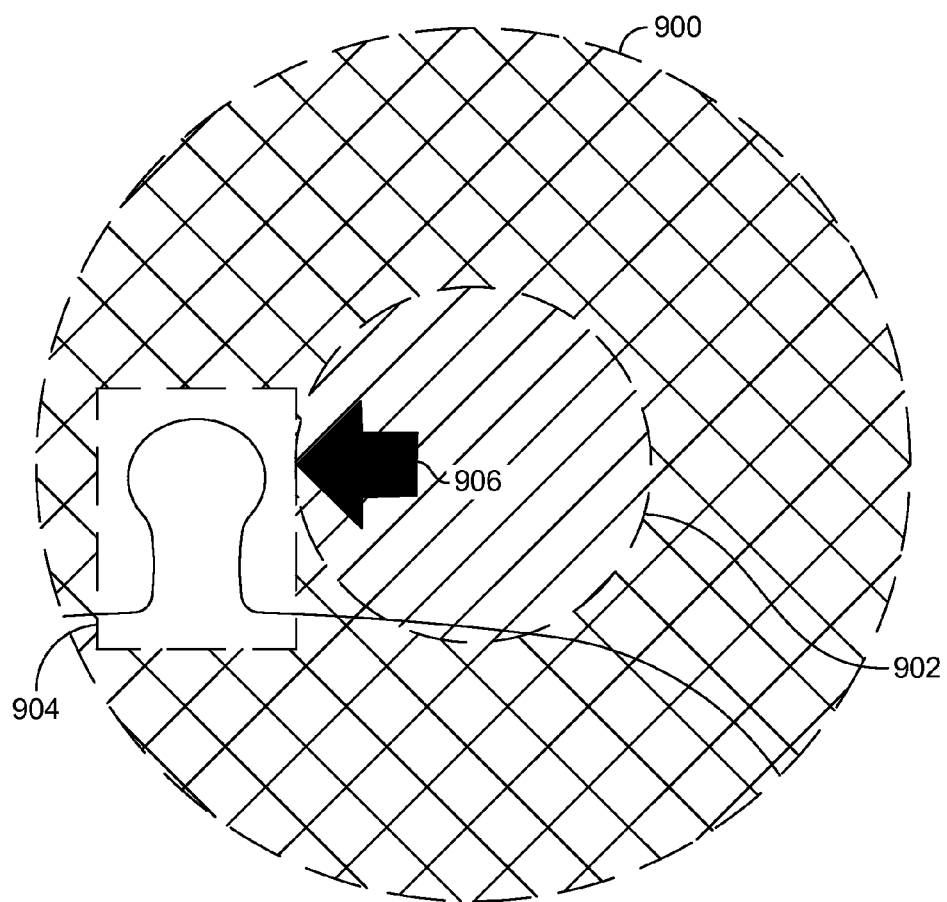
FIG. 9 is a diagram illustrating providing a directional maker in displayed portion of an overall FOV to indicate a location of an area of interest outside of the displayed portion.

Alternatively, if the entire area of interest is outside the displayed portion, the presence of the area of interest may be brought to the endoscopist's attention, as shown at block 814. This may be done in a number of different ways in accordance with various embodiments of the present invention. In some embodiments, a directional indication may be displayed to the endoscopist that indicates a possible lesion has been identified and the location of the possible lesion relative to the current displayed view. For instance, as shown in FIG. 9, a camera with an overall FOV 900 is employed with only a portion 902 displayed to the endoscopist. An area of interest 904 has been detected by the system. Based on the detection, a directional arrow 906 is displayed to the endoscopist. As such, the endoscopist may move the endoscope to bring the area of interest within the displayed portion. If this occurs, the system may detect that the area of interest is now within the displayed portion, and the area of interest may be visually marked on the display.

Figure 10A:
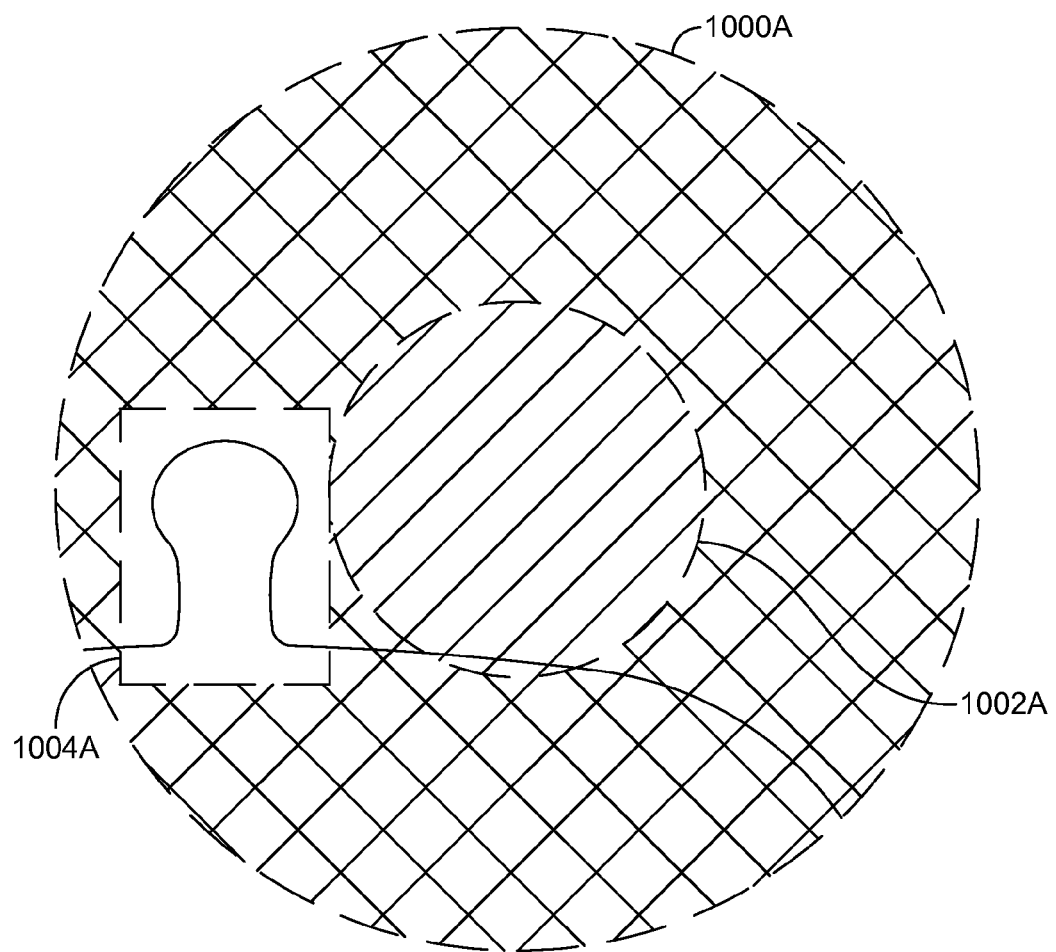
FIGS. 10A and 10B are diagrams illustrating changing a displayed portion of an overall FOV to locate an identified area of interest within the displayed portion.
Figure 10B:
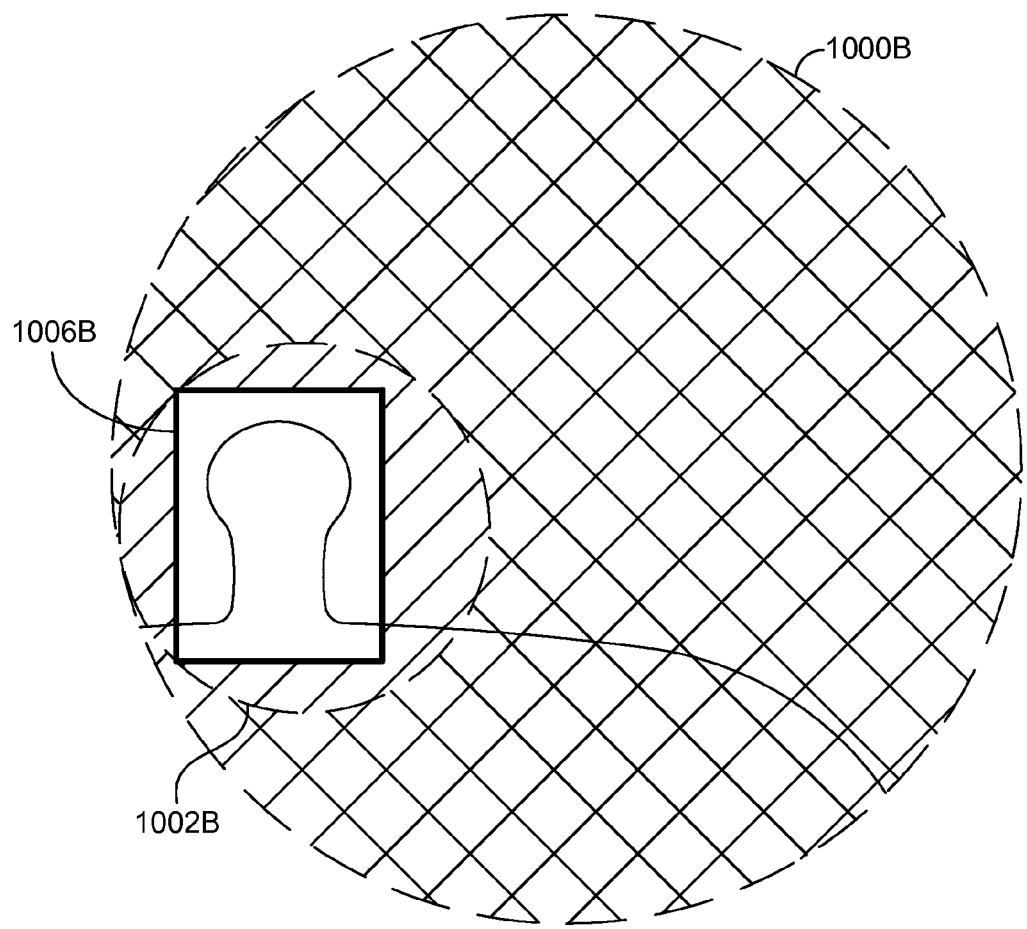

Another approach to facilitating an endoscopist in viewing an area of interest identified by the system that is outside the displayed portion may be to change the displayed portion of the overall FOV without requiring the endoscopist to move the endoscope. For instance, as shown in FIG. 10A, an area of interest 1004A has been detected in an area of the overall FOV 1000A outside of the displayed portion 1002A. As shown in FIG. 10B, the displayed portion 1002B has been moved to include the area of interest 1004B. As such, the endoscopist can now view the area of interest, which has been visually marked on the display. As an alternative (or in addition to) changing the displayed portion of the overall FOV, the endoscope may have mechanical controls that may allow the camera to be automatically moved. Accordingly, the system may employ these controls to move the camera until the area of interest is within the displayed portion of the FOV.

The change in the portion of overall FOV that is displayed may be automatic or manual. For instance, in some embodiments, when the system detects an area of interest in the overall FOV outside the displayed portion, the system may automatically change the displayed portion to display the identified area of interest. However, this movement may be disorienting to the endoscopist. Accordingly, in some embodiments, the system may display a message to the endoscopist indicating that a possible lesion has been detected and provide an option to view the identified area of interest. The endoscopist may then decide whether to select to view the area of interest. If selected, the displayed portion of the overall FOV may be changed to include the identified area of interest. This may include gradually moving the displayed portion from the previous location until the area of interest is within the displayed portion.

In some cases, an identified area of interest may be partially inside the displayed portion and partially outside the displayed portion. As shown at block 816, the detected area of interest in this case is brought to the endoscopist's attention. This may be done in a number of different ways. For example, in some cases, the portion of the area of interest within the displayed portion of the overall FOV is visually marked. Based on this marking, the endoscopist may then decide to move the endoscope to bring the entire area of interest within view. In other cases, the presence of the area of interest may be brought to the endoscopist's attention by providing additional information. This may include a directional arrow indicating the location of the area of interest relative to the displayed portion. This could also include a message that an area of interest has been identified, and the endoscopist may be given an option to select to view the area of interest which may cause the displayed portion of the overall FOV to be changed to bring the area of interest within the displayed portion and/or mechanical controls to be employed to automatically move the camera to bring the area of interest within the displayed portion.

Another use of the larger FOV that may be employed in accordance with some embodiments of the present invention is for image stabilization purposes. Traditionally, during endoscopic procedures, after a possible lesion has been detected, it's possible the endoscope may move around causing the possible lesion to move partially or entirely out of view. In accordance with some embodiments of the present invention, a larger FOV may be employed and the displayed portion of the overall FOV may be moved to keep an identified area of interest within the display being viewed by the endoscopist.

Figure 11:
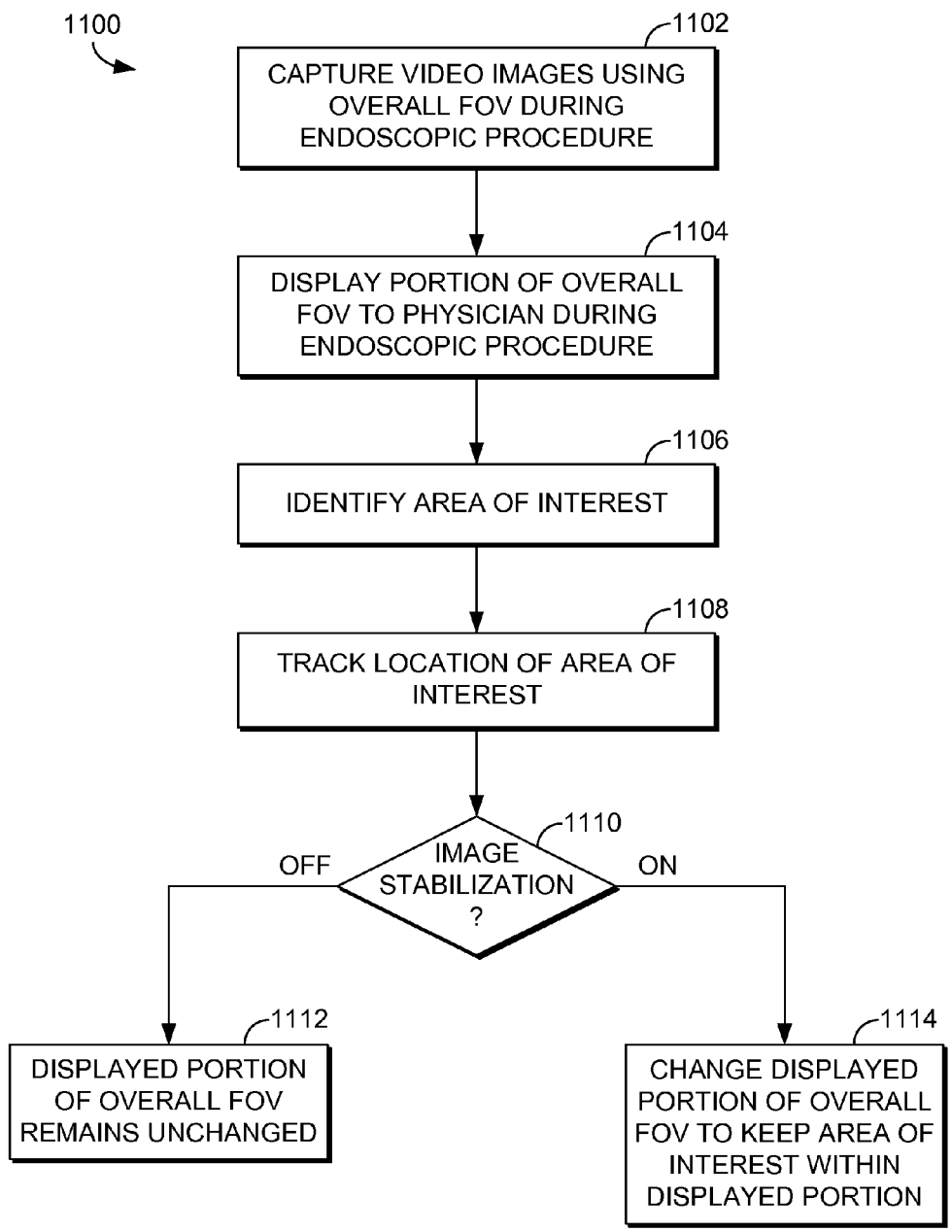
FIG. 11 is a flow diagram showing a method for moving a displayed portion of an overall FOV for image stabilization purposes in accordance with an embodiment of the present invention.

Referring to FIG. 11, a flow diagram is provided that illustrates a method 1100 for moving a displayed portion of an overall FOV for image stabilization purposes in accordance with an embodiment of the present invention. As shown at block 1102, video images are captured using a camera with an overall FOV during an endoscopic procedure. In some embodiments, this overall FOV may be greater than 170 degrees and may be 220 degrees in some particular embodiments. A portion of the overall FOV is displayed to the endoscopist in real-time or near real-time during the endoscopic procedure, as shown at block 1104. In some embodiments, this may be the center portion of the overall FOV (e.g., as shown in FIG. 7B).

An area of interest is identified, as shown at block 1106. The area of interest may be identified automatically by the system and/or manually by the endoscopist. The system tracks the identified area of interest as shown at block 1108 by repeatedly analyzing the video images from the endoscope.

A determination is made regarding whether image stabilization is turned on, as shown at block 1110. For instance, the system may be configured to allow the endoscopist to turn the image stabilization on or off. If turned off, the displayed portion of the overall FOV may remain unchanged as the camera is moved relative to the area of interest, as shown at block 1112. If the area of interest moves outside the displayed portion, relocation techniques may be employed, such as providing a visual indication of where the area of interest is located relative to the camera view as described above.

Figure 12A:
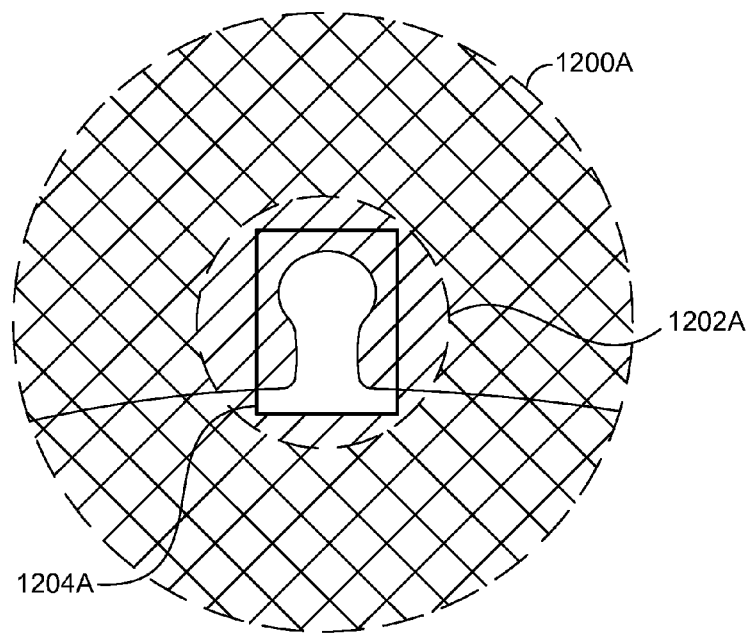
FIGS. 12A and 12B are diagrams illustrating image stabilization by changing a displayed portion of an overall FOV to maintain an area of interest within the displayed portion as the area of interest moves relative to an endoscope.
Figure 12B:
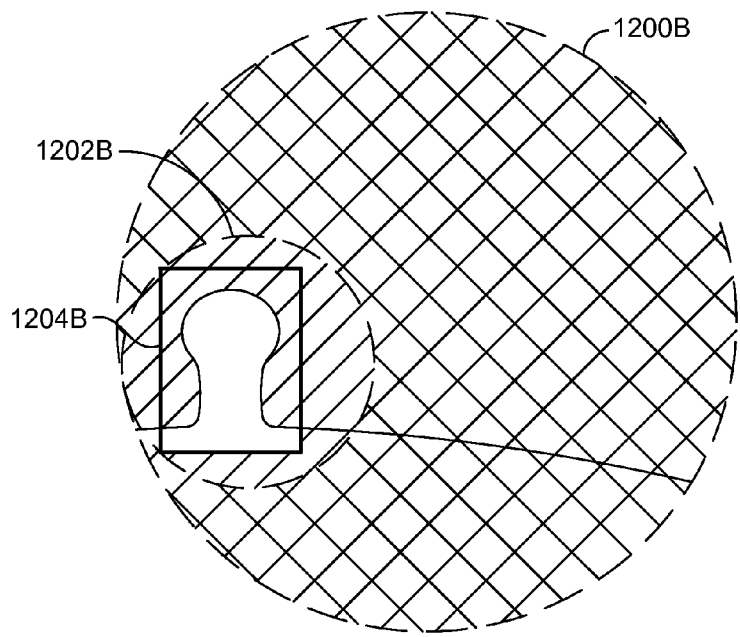

Alternatively, if image stabilization is turned on, the system operates to change the displayed portion of the FOV to keep the area of interest within the displayed portion as the camera moves relative to the area of interest, as shown at block 1114. In particular, the system continues to analyze the video images from the endoscope to track the location of the area of interest. As the area of interest moves, the location of the area of interest is tracked and the displayed portion of the overall FOV is changed such that the area of interest remains within the display being viewed by the endoscopist. This is illustrated by way of example in FIGS. 12A and 12B. Initially, as shown in FIG. 12A, an area of interest 1204A has been marked within the displayed portion 1202A, which is near the center of the overall FOV 1200A. As shown in FIG. 12B, the area of interest 1204B has moved relative to the camera, and the displayed portion 1202B has been automatically changed to keep the area of interest 1204B within the displayed portion 1202B.

In some cases, the area of interest may move outside the overall FOV when image stabilization is turned on. If that occurs, relocations techniques may be employed, such as providing a directional indicator to indicator to the endoscopist which direction to move the endoscope camera to relocate the area of interest, as described above.

Endoscope Navigation

Navigating a flexible endoscope through the lumen (i.e., hollow center) of an organ is typically performed during an endoscopic procedure to advance the endoscope. The more frequently the endoscope end is kept near the center of the lumen, the more quickly the scope can be advanced, and the more symmetrically the anatomy is viewed. Accordingly, some embodiments employ techniques to maintain the endoscope near the center of the lumen and/or otherwise assist in navigating the endoscope in a patient's organ.

Figure 13:
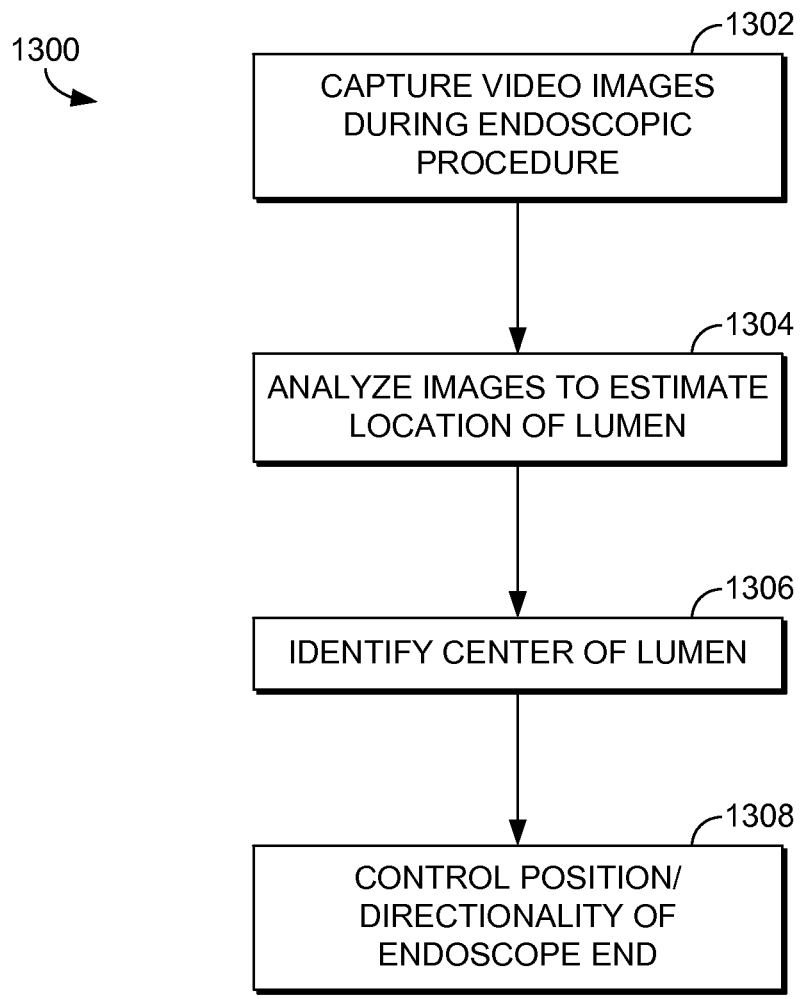
FIG. 13 is a flow diagram showing a method for a system controlling an endoscope to maintain an endoscope camera near the center of a lumen during an endoscopic procedure in accordance with an embodiment of the present invention.

In some embodiments, computer vision techniques may be employed by the system to identify the lumen, and mechanical controls on the endoscope may be automatically controlled by the system to maintain the camera end of the endoscope near the center of the lumen. Turning to FIG. 13, a flow diagram is provided that illustrates a method 1300 of a system controlling an endoscope to maintain an endoscope camera near the center of a lumen during an endoscopic procedure in accordance with an embodiment of the present invention. As shown at block 1302, video images are captured using an endoscope during an endoscopic procedure on a patient. Video images are analyzed by the system in real-time or near real-time during the endoscopic procedure to estimate the location of the lumen in the patient's organ, as shown at block 1304. This may include, for instance, analyzing the images by using edge detection to identify the edges of the organ and a circular shape within the edges. A center of the lumen is determined based on this analysis, as shown at block 1306. The system employs mechanical controls on the endoscope end to adjust the position/direction of the endoscope end to maintain the endoscope end near the center of the lumen, as shown at block 1308. This process may be repeated as the endoscope is advanced through the patient's organ to maintain the endoscope near the center of the lumen.

Figure 14:
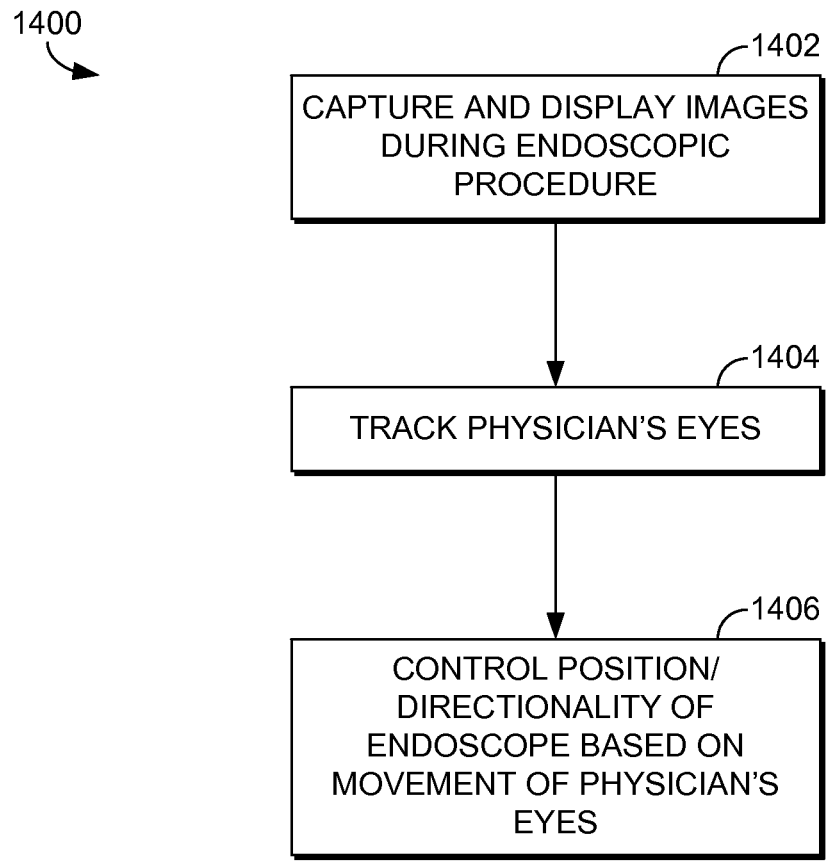
FIG. 14 is a flow diagram showing a method for using an endoscopist's eye position/movement to control an endoscope during an endoscopic procedure in accordance with an embodiment of the present invention.

In further embodiments, the position/direction of the endoscope end may be automatically controlled by the system based on the endoscopist's eye positions while watching the video display. FIG. 14 provides a flow diagram illustrating a method 1400 for using an endoscopist's eye position/movement to control an endoscope during an endoscopic procedure in accordance with an embodiment of the present invention. As shown at block 1402, video images are captured and displayed in real-time or near real-time during an endoscopic procedure. As the procedure continues and the endoscope is advanced, the endoscopist watches the display. The system tracks the endoscopist's eyes looking at the display, as shown at block 1404. Any of a variety of known head and/or eye tracking technologies may be employed. Based on the endoscopist's eye movements, the system controls the position/directionality of the endoscope end, as shown at block 1406. For instance, as the endoscope is advanced during an endoscopic procedure, if the center of the lumen shifts left, the endoscopist's eyes are likely to follow it. By tracking the endoscopist's eyes, the position/directionality of the endoscope end may be adjusted to the left, resulting in the endoscope end remaining in the center of the lumen.

The auto-centering approach discussed above with reference to FIG. 13 and the eye-tracking approach discussed above with reference to FIG. 14 may be employed individually or in cooperation to assist an endoscopist during an endoscopic procedure. Additionally, the technologies could be toggled off by the endoscopist to allow for fully manual navigation when it is desired (e.g., when the endoscopist no longer desires to keep the endoscope end centered in the lumen).

Modeling and Visualization

Further embodiments are directed to stitching together multiple images (i.e., frames) captured by an endoscope to create a photo-realistic model of the anatomy of a patient's organ. Generally, images may be captured by an endoscope during an endoscopic procedure. Those images may be stitched together using known image stitching technology to generate the photo-realistic model of the patient's organ.

The model created may be used for a number of different purposes. In some embodiments, a graphical representation of the anatomy may be constructed and employed to determine portions of the anatomy that were not imaged. This may be done in real-time or near real-time during an endoscopic procedure and displayed to the endoscopist to allow the endoscopist to view the areas that have not been completely imaged. This provides an opportunity for the endoscopist to go back and image those areas in order to provide a more complete endoscopic visualization of an organ, which supports greater detection of lesions.

Information regarding areas not imaged during an endoscopic procedure may also be useful after the procedure. For instance, statistics regarding the percentage of the organ imaged may be generated. This information may be collected over a number of procedures and used for reporting and benchmarking purposes. For instance, the information could indicate how much each endoscopist is imaging on average. As such, endoscopists who aren't sufficiently imaging patient's organs may be identified, and the statistics may provide objective evidence of needs for improved performance. Re-education may be employed to increase the amount being imaged. In some instances, this may include using statistics from previous endoscopic procedures to identify the particular needs for improvement. For example, an endoscopist may routinely miss a particular area of a colon when performing a colonoscopy. This may become evident from the modeling information. The endoscopist may review the information and make efforts to better image that particular area when performing future colonoscopies.

The graphical representation may also be used to denote the relative locations of identified areas of interest (e.g., areas containing lesions). For instance, when an area of interest is identified, metadata that includes the location of the area of interest within the graphical representation may be stored. Information regarding the location of the area of interest may be used, for instance, during an endoscopic procedure to relocate a lesion, for instance by displaying the photo-realistic graphical representation of the patient's organ with areas of interest visually marked. The location of an area of interest may also be used after the endoscopic procedure in which the area was located. For instance, the location information may be employed in preparation for and/or during a subsequent procedure to assist the endoscopist in relocating the area of interest. As another example, the graphical representation with identified areas of interest could be used for post-procedure analyses. For instance, the graphical representation with location information stored for an identified area of interest may be provided to a pathologist with a biopsy sample taken from the area of interest. As such, the pathologist may navigate the graphical representation of the anatomy to view the area of interest when analyzing the biopsy.

As can be understood, the present invention provides techniques to assist endoscopists in identifying and tracking lesions during endoscopic procedures. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that embodiments of this invention are well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media storing computer usable instructions that, when used by one or more computing devices, cause the one or more computing devices to perform operations comprising:
   identifying an area of interest of a patient's organ within images captured by an endoscope during an endoscopic procedure;
   providing a visual marker identifying the area of interest within displayed images of a camera view being viewed by an endoscopist;
   tracking a location of the area of interest relative to the camera view during the endoscopic procedure;
   determining the location of the area of interest has changed relative to the camera view;
   determining if the area of interest remains within the camera view;
   if the area of interest remains within the camera view, moving the visual marker based on the change in the location of the area of interest;
   if the area of interest has moved outside of the camera view, providing a visual directional marker based on the location of the area of interest relative to the camera view;
   tracking the endoscopist's eyes looking at the displayed images of the camera view; and
   based on movements of the endoscopist's eyes, controlling a directionality of the endoscope.

2. The one or more computer storage media of claim 1, wherein the area of interest is manually identified by an endoscopist.

3. The one or more computer storage media of claim 2, wherein the area of interest is manually identified by the endoscopist by:
   receiving input from an endoscopist via an input device marking an area within the displayed images as the area of interest.

4. The one or more computer storage media of claim 1, wherein the area of interest is automatically identified.

5. The one or more computer storage media of claim 4, wherein the area of interest is automatically identified by:
   providing a library of lesion shapes;
   performing edge detection to determine a shape of an area within the patient's organ;
   comparing the shape with the library of lesion shapes;
   determining the shape as matching a lesion shape from the library of lesion shapes; and
   identifying the area as an area of interest based on the shape matching the lesion shape from the library of lesion shapes.

6. The one or more computer storage media of claim 4, wherein the area of interest is automatically identified by:
   presenting the images in white light to the endoscopist;
   analyzing the images using modified color conditions as a background process; and
   identifying the area of interest based on analysis of the images using the modified color conditions.

7. The one or more computer storage media of claim 6, wherein the operations further comprise: changing the images displayed to the endoscopist to modified color images based on a modified color channel setting used to identify the area of interest.

8. The one or more computer storage media of claim 1, wherein the visual marker comprises at least one selected from the following: a box surround the area of interest, highlighting an edge of the area of interest, coloring the area of interest, and dimming areas outside of the area of interest.

9. The one or more computer storage media of claim 1, wherein tracking the location of the area of interest relative to a camera view during the endoscopic procedure comprises employing computer vision techniques to analyze images captured during the endoscopic procedure to determine movement of the area of interest relative to the camera view.

10. A method in a clinical computing environment for tracking an area of interest of a patient's organ during an endoscopic procedure, the method comprising:
    identifying the area of interest within a camera view of an endoscope during the endoscopic procedure;
    determining the area of interest has moved outside the camera view during the endoscopic procedure;
    displaying a directional indication on displayed images identifying a location of the area of interest relative to the camera view during the endoscopic procedure;
    tracking the endoscopist's eyes looking at the displayed images of the camera view; and
    based on movements of the endoscopist's eyes, controlling a directionality of the endoscope.

11. The method of claim 10, wherein identifying the area of interest comprises receiving input from an endoscopist via an input device marking an area within the displayed images as the area of interest.

12. The method of claim 10, wherein the area of interest is automatically identified by:
    providing a library of lesion shapes;
    performing edge detection to determine a shape of an area within the patient's organ;
    comparing the shape with the library of lesion shapes;
    determining the shape as matching a lesion shape from the library of lesion shapes; and
    identifying the area as an area of interest based on the shape matching the lesion shape from the library of lesion shapes.

13. The method of claim 10, wherein the area of interest is automatically identified by:
    presenting the displayed images in white light to the endoscopist;
    analyzing captured images using modified color conditions as a background process; and
    identifying the area of interest based on analysis of the captured images using the modified color conditions.

14. The method of claim 13, wherein the method further comprises: changing the displayed images to modified color images based on a modified color channel setting used to identify the area of interest.

15. The method of claim 10, wherein the method further comprises displaying a visual marker identifying the area of interest on the displayed images when the area of interest is within the displayed images, the visual marker comprising at least one selected from the following: a box surround the area of interest, highlighting an edge of the area of interest, coloring the area of interest, and dimming areas outside of the area of interest.

16. The method of claim 10, wherein determining the area of interest has moved outside the camera view during the endoscopic procedure comprises employing computer vision techniques to analyze images captured during the endoscopic procedure to determine movement of the area of interest relative to the camera view.

17. A system in a clinical computing environment for tracking an area of interest of a patient's organ during an endoscopic procedure, the system comprising:
- one or more processors; and
- one or more computer storage media storing instructions to cause the one or more processors to:
- identify the area of interest within a camera view of an endoscope during the endoscopic procedure,
- determine the area of interest has moved outside the camera view during the endoscopic procedure,
- display a directional indication on displayed images identifying a location of the area of interest relative to the camera view during the endoscopic procedure,
- tracking the endoscopist's eyes looking at the displayed images of the camera view, and
- based on movements of the endoscopist's eyes, controlling a directionality of the endoscope.

18. The system of claim 17, wherein the area of interest is manually identified by an endoscopist.

19. The system of claim 17, wherein the area of interest is automatically identified by the system analyzing images captured during the endoscopic procedure.

20. The system of claim 17, wherein determining the area of interest has moved outside the camera view during the endoscopic procedure comprises employing computer vision techniques to analyze images captured during the endoscopic procedure to determine movement of the area of interest relative to the camera view.

* * * * *